(12) United States Patent
Sinn et al.

(10) Patent No.: US 6,812,209 B1
(45) Date of Patent: Nov. 2, 2004

(54) CONJUGATE CONSISTING OF AN ACTIVE SUBSTANCE AND A NON-EXOGENOUS NATIVE PROTEIN

(75) Inventors: Hansjörg Sinn, Wiesloch (DE); Hans-Hermann Schrenk, Zeiskam (DE); Wolfgang Maier-Borst, Dossenheim (DE); Gerd Stehle, Ehingen (DE); Andreas Wunder, Eppelheim (DE); Dirk Hoff-Biederbeck, Ludwigshafen (DE); Dieter Ludwig Heene, Mannheim (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 0 days.

(21) Appl. No.: 09/640,838

(22) Filed: Aug. 16, 2000

Related U.S. Application Data

(63) Continuation of application No. 08/817,185, filed as application No. PCT/DE95/01323 on Sep. 22, 1995, now abandoned.

(30) Foreign Application Priority Data

Sep. 22, 1994 (DE) .......................................... 44 33 890

(51) Int. Cl.$^7$ .............................................. A61K 38/00
(52) U.S. Cl. .............................. 514/12; 514/2; 530/363
(58) Field of Search .......................... 530/391.9, 391.3, 530/362–365; 514/2, 12, 150, 155, 152; 424/178.1, 179.1, 194.1, 130.1

(56) References Cited

U.S. PATENT DOCUMENTS

| | | | | |
|---|---|---|---|---|
| 3,976,763 A | * | 8/1976 | Spector | ...................... 424/1.5 |
| 4,456,691 A | | 6/1984 | Stark | |
| 4,522,750 A | * | 6/1985 | Ades et al. | |
| 4,731,439 A | * | 3/1988 | Marquardt et al. | |
| 5,066,789 A | * | 11/1991 | Srinivasan et al. | ......... 530/388 |
| 5,116,944 A | * | 5/1992 | Sivam et al. | |
| 5,169,934 A | * | 12/1992 | Clark et al. | |

FOREIGN PATENT DOCUMENTS

| | | |
|---|---|---|
| BE | 882 541 | 7/1980 |
| DE | 41 22 210 | 1/1993 |
| WO | WO 91/18012 | 11/1991 |
| WO | WO 94/27641 | 12/1994 |

OTHER PUBLICATIONS

Blair, A.H. and Ghose, T.I., Journal of immunological Methods, 59: 129–143, 1983.*
Sezaki et al., Critical Reviews in Therapeutic Drug Carrier Systems, 1(1): 1–38–1984.*
Oseroff, A.R. et al, Proc. Natl. Acad. Sci, USA 83(22): 8744–8748; abstract only.*
Wong, Chemistry of Protein Conjugation and Cross–Linking, CRC Press, Inc. pp. 63–67 (1991).*
Hamblin, M. R. and E. L. Newman, 1994, "Photosensitizer Targeting in Photodynamic Therapy: I. Conjugates of Haematoporphyrin With Albumin and Transferrin", *J. Photochem. Photobiol. B: Biology* 26:45–56.
Henriksen, U. and O. Buchardt, 1991, "Azidobenzoyl–, azidoacridinyl–, diazocyclopentadienylcarbonyl– and 8–propyloxypsoralen photobiotinylation reagents. Sytheses and photoreactions with DNA and protein", *J. Photochem. Photobiol. A: Chem.* 57:331–342.
Fiume et al., Jul. 2, 1988, "Inhibition of Hepatitis B Virus Replication by Vidarabine Monophosphate Conjugated with Lactosaminated Serum Albumin", *The Lancet.* 13–15.
Fujiwara, K., et al., "Development of Enzyme Immunoassay for Chromomycin $A_3$ and Olivomycin Using β–D–Galactosidase as a Label$^1$," Cancer Res. (1985) 45:5442–5446 (Nagasald Univ. Pharmaceutical Sciences, Japan).
Basu, S.K., "Receptor–Mediated Endocytosis of Macromolecular Conjugates in Selective Drug Delivery," Biochem. Pharma. (1990) 40(9):1941–1946 (0006–2952/90).

* cited by examiner

*Primary Examiner*—Sheela J. Huff
(74) *Attorney, Agent, or Firm*—Dorsey & Whitney LLP; Birgit Millauer

(57) ABSTRACT

This invention relates to a conjugate which consists of an active substance and a native protein which is not regarded as exogenous and distinguish itself in that an intracellulary cleavable linker is present between the active substance and the protein.

In addition, this invention concerns a process for the preparation of such a conjugate and its use.

25 Claims, 4 Drawing Sheets

CONJUGATE CONSISTING OF AN ACTIVE SUBSTANCE AND A NON-EXOGENOUS NATIVE PROTEIN

This application is a continuation of Application Ser. No. 08/817,185, filed Sep. 23, 1997, now abandoned, which is a national phase filing of the Application No. PCT/DE95/01323, which as filed with the Patent Cooperation Treaty on Sep. 22, 1995, and is entitled to priority of the German Patent Application P 44 33 890.2, filed Sep. 22, 1994.

I. FIELD OF THE INVENTION

This invention relates to a conjugate consisting of an active substance and a native protein which is not regarded as exogenous, a process for the preparation of such a conjugate as well as its use.

II. BACKGROUND OF THE INVENTION

For a long time there has been a great demand to transport in well-calculated fashion pharmaceutical preparations to certain sites within the body where they are allowed to display their activity. The former has been achieved by an above conjugate. See, DE-41 22 210. It serves for concentrating a tumor-active compound in the tumor.

Surprisingly, it has now turned out that an above conjugate is also highly active when an intracellularly cleavable linker is present between the active substance and the native protein which is not regarded as exogenous.

Such a conjugate represents the subject matter of the present invention.

III. SUMMARY OF THE INVENTION

This invention relates to a conjugate which consists of an active substance and a native protein which is not regarded as exogenous and distinguishes itself in that an intracellularly cleavable linker is present between the active substance and the protein.

In addition, this invention concerns a process for the preparation of such a conjugate and its use.

IV. BRIEF DESCRIPTION OF THE DRAWINGS

V. DETAILED DESCRIPTION OF THE INVENTION

Figure 1:
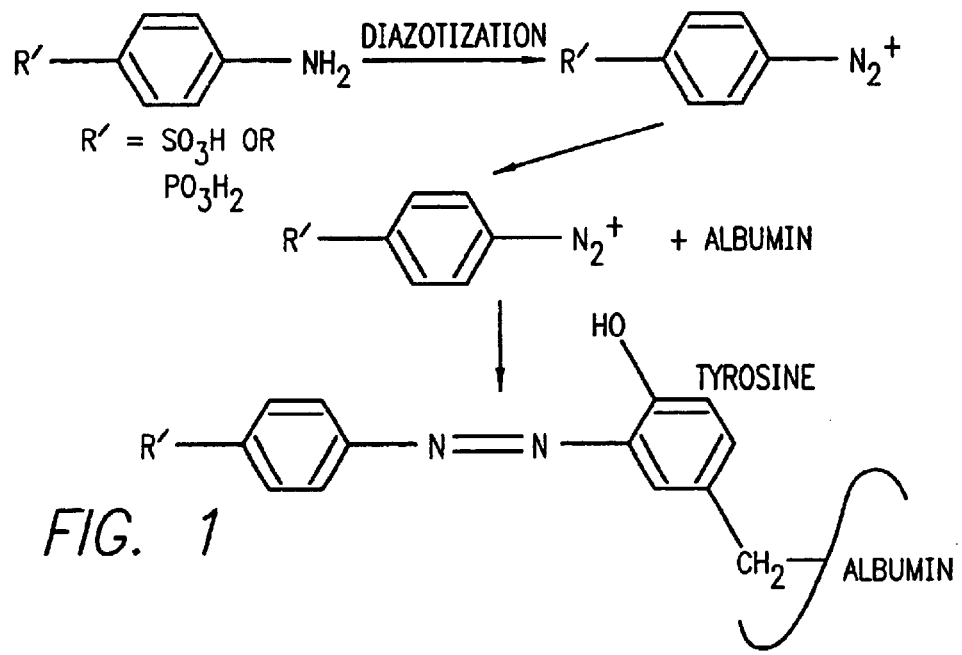
FIG. 1 shows the binding of 4-aminophenylsulphonic acid or 4-aminophenylphosphonic acid to albumin, an azo group being present as linker.

The above expression "active substance" comprises compounds of any kind which can be used for treating a disease. They are, e.g., compounds for treating tumoral, infectious and/or autoimmune diseases. Examples of such compounds are chemotherapeutic agents such as antibiotics, e.g., tetracyclines, and antimetabolites, e.g., methotrexate, sulphonamides and nucleosides which after the incorporation into a nucleic acid inhibit its replication and transcription, respectively. Preferred compounds of the above kind are those which have an acid group such as —$CO_2H$, —$SO_3H$, —$PO_3H_2$, or —$AsO_3H_2$. Especially preferred compounds are 4- and 2-aminobenzoic acid, 4- and 2-aminophenylsulphonic acid, 4- and 2-aminophenylphosphonic acid, 4- and 2-aminophenylarsonic acid as well as derivatives thereof. Further preferred compounds are deoxyuridine (UDR), deoxycytidine (CDE), cytosine arabinoside (AraC), 5-fluorouracil (5-FU), 5-fluorodeoxyuridine (5-FUDR), azidothymidine (AZT).

Further examples of compounds as active substance are photoactive substances such as porphyrines, chlorines and bacteriochlorines which can be used for the photodynamic treatment.

One or several of the above compounds are present in a conjugate according to the invention. They are given as educts, which means that they are present in derivatized form in a conjugate according to the invention. See, Examples 1–7 and FIGS. 1–3, infra.

An above active substance is linked via a linker to a protein. This protein is not considered exogenous by the body. It is also available in native, i.e., non-modified, form. In addition, the protein has a molecular weight (MW) of up to 90,000, preferably it is an albumin, particularly human serum albumin, or transferrin.

An above linker can be cleaved intracellularly. The expression "cell" comprises individual cells and cell aggregates. Examples of the former are endogenous cells which are not present in an aggregate, e.g., blood cells and virus-infected cells, and exogenous cells, e.g., microorganisms such as bacteria, fungi and protozoa. Cell aggregates comprise tissues, organs and tumors.

A person skilled in the art is familiar with a linker of the above kind. He is also familiar with factors, e.g., enzymes, which cause the cleavage of certain chemical bonds in cells. Thus, he can construct further linkers which can be cleaved intracellularly. Such a linker favorably comprises an azo group, which is preferably cleaved. The following structure of the linker is especially favorable: wherein

R is an organic group, preferably an aromatic one, and especially preferably phenylene or a derivative thereof, and Y is a group selected from C(O), S(O)$_2$, P(O)OH and As(O)OH.

The above structure of a preferred linker corresponds to that which the linker has in a conjugate according to the invention. Furthermore, at least when R is phenylene or a derivative thereof, the structure comprises an active compound which is especially suited for treating tumoral, infectious and autoimmune diseases. Having cleaved the linker and optionally degraded the protein still linked to the linker, the compound can display its full activity. See, Examples 3 to 7 and FIGS. 2 and 3, infra.

Figure 2A:
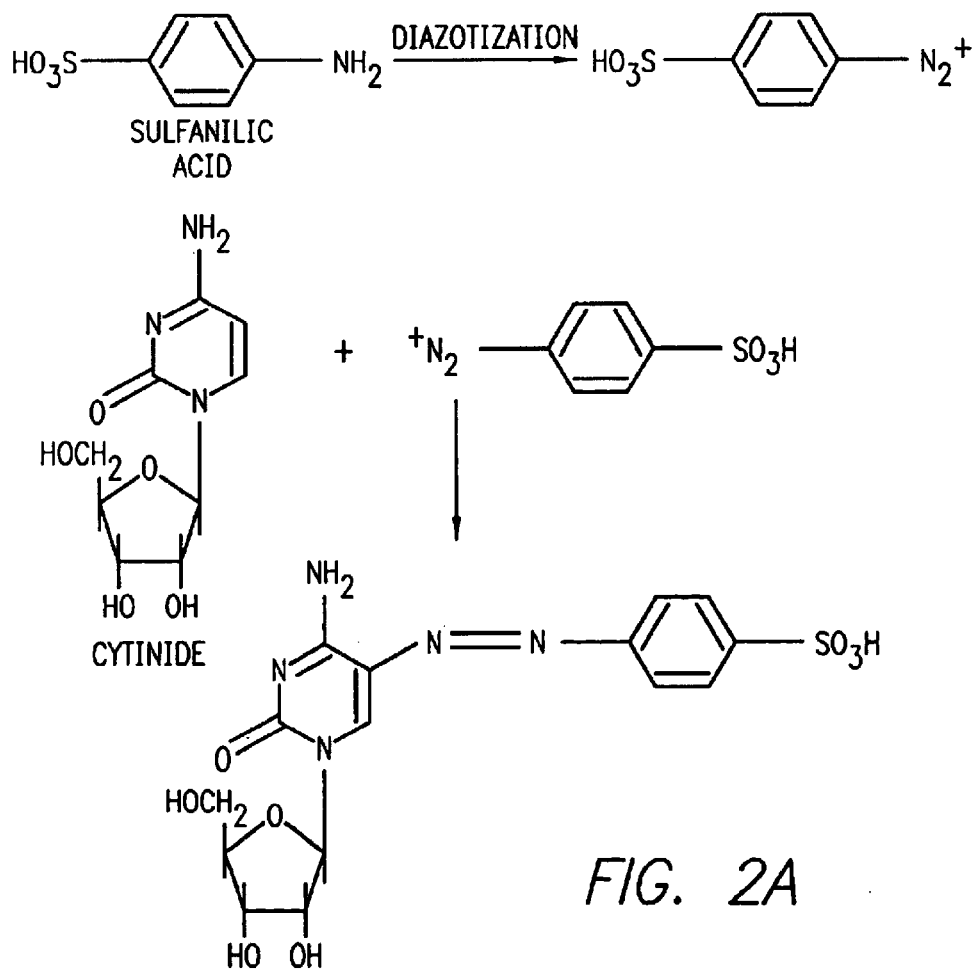
FIG. 2 shows the binding of cytidine to albumin, a linker containing an azo group being present, and the release of aminocytidine.
Figure 2B:
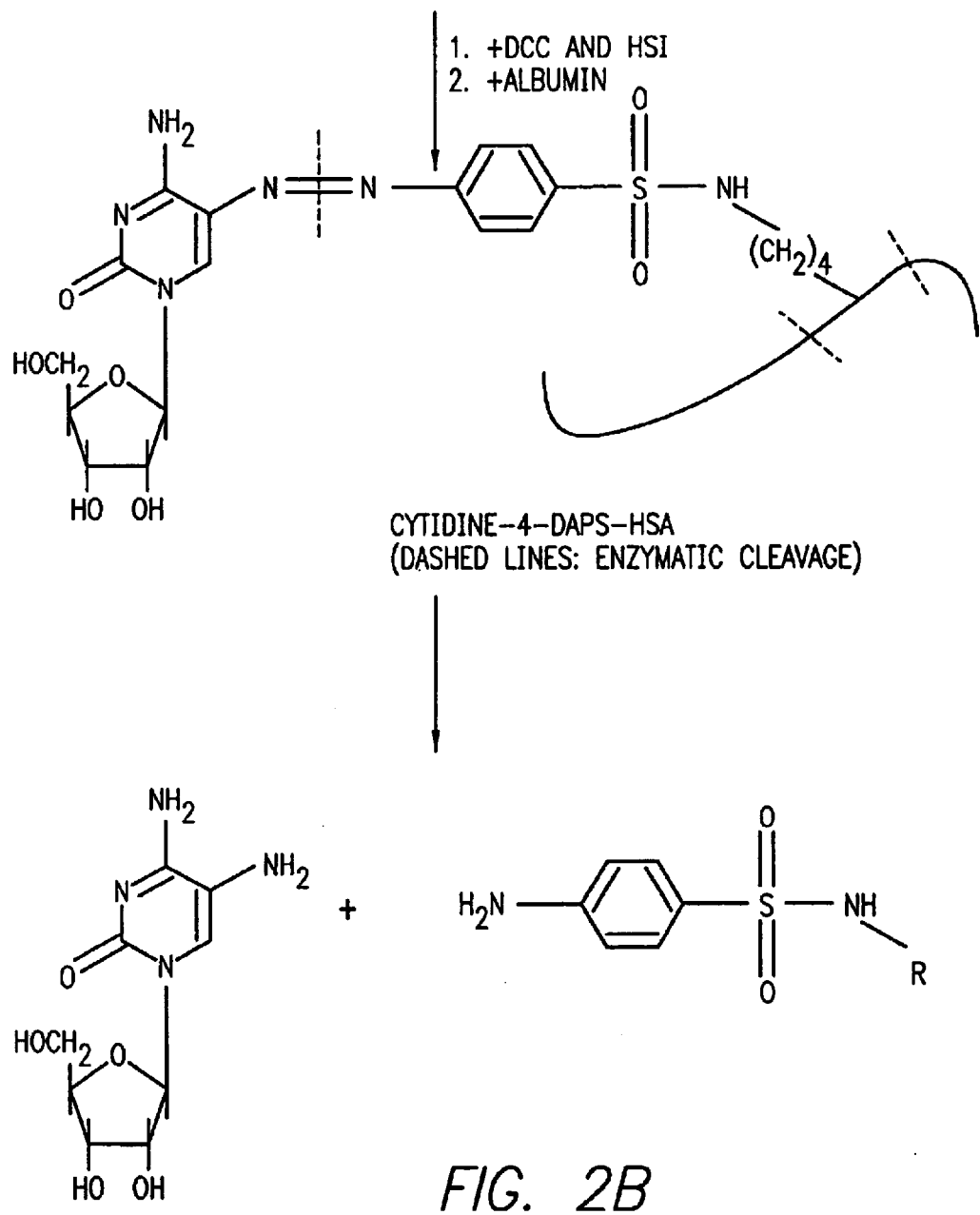
Figure 3:
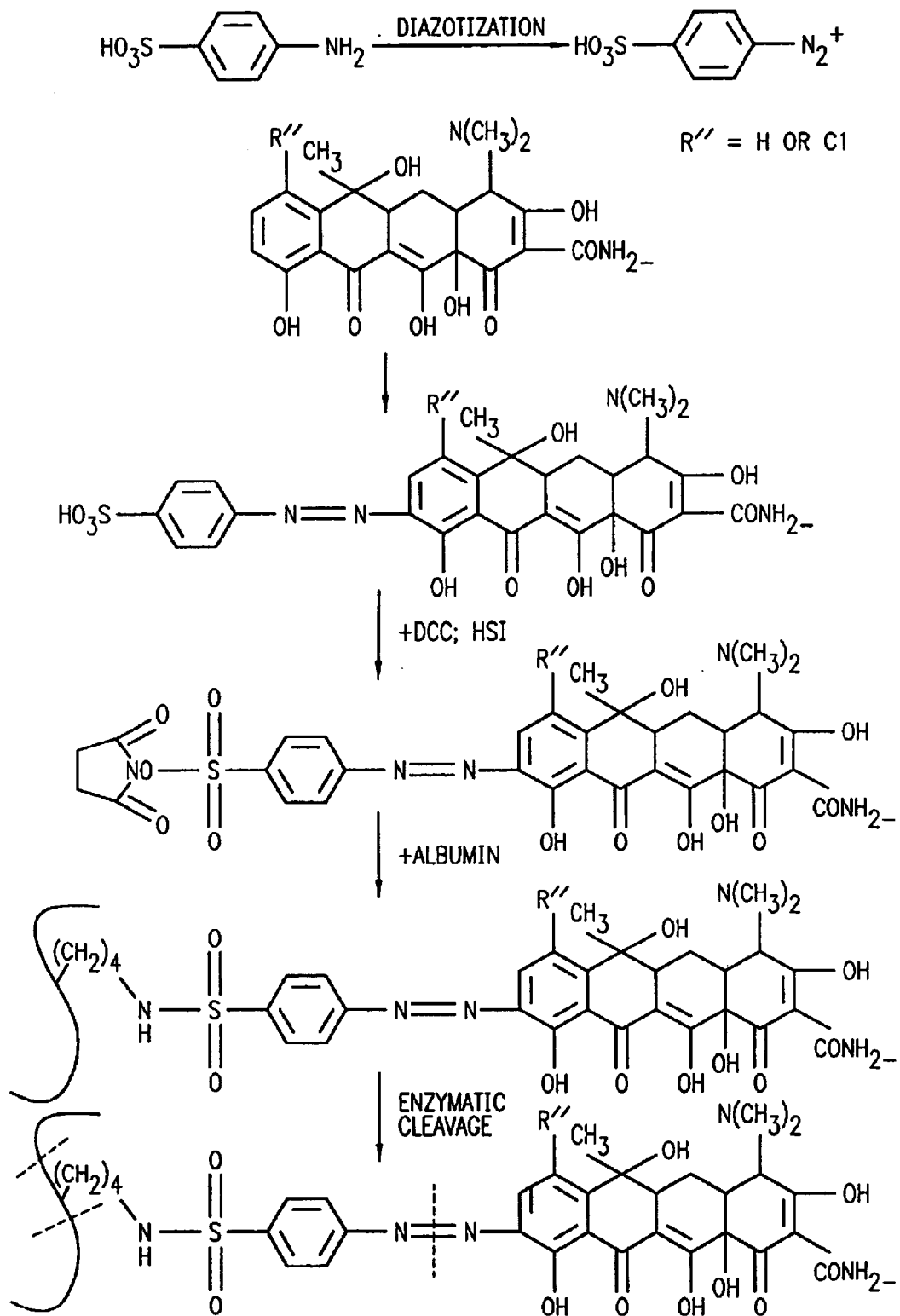
FIG. 3 shows the binding of tetracycline to albumin, a linker containing an azo group being present.

Preferred conjugates of the present invention are shown in FIGS. 1 to 3.

A process for the preparation of an above conjugate is also provided according to the invention. In such a process, conventional reactions occurring in chemistry such as diazotizing of an amino group and activation of an acid group, are used individually or in combination. Reference is made to the preparation of the conjugates in Examples 1 to 7 and FIGS. 1 to 3.

Conjugates according to the invention distinguish themselves in that they concentrate active substances in well-calculated fashion in certain cells of the body and allow them to fully display their activity. This is achieved by a combination consisting of a protein, e.g., albumin, and an intracellularly cleavable linker. Certain cells in the body, particularly tumor cells, cells of flammable tissues and microorganisms, preferably absorb albumin and because of their enzymes cleave the linker-active substance conjugate, so that the active substance and substances, respectively, is (are) released and can fully display its (their) activity.

Thus, conjugates according to the invention are suited in the best possible manner for therapeutic purposes, particularly for treating tumoral, infectious and autoimmune diseases.

In addition, labelings (e.g., radioactive labelings) may exist in conjugates according to the invention, so that the conjugates can also be used for diagnostic purposes and therapy control, optionally simultaneously for treatment.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Preparation Of A Conjugate According To The Invention Consisting Of Human Serum Albumin And 4-Aminophenylsulphonic Acid, An Azo Group Being Present As Linker The preparation of the conjugate and its structure are shown in FIG. 1.
1. Diazotization of 4-aminophenylsulphonic acid:
   4-Aminophenylsulphonic acid (173 mg, 1. mmole) was dissolved in 5 ml 2 N HCl. The solution was cooled in an ice bath, and 600 µl of an ice-cooled 2.5 M NaNO$_2$ solution (1.5 mmoles) were added in portions of 0.1 ml each with constant stirring. After about 10 min, the excess of nitrite was eliminated by the addition of urea. 4-Diazoniumphenylsulphonic acid (4-DAPS) was obtained.
2. Linkage of 4-DAPS to human serum albumin (HSA):
   The 4-DAPS solution obtained under item 1, was slowly added to a solution of 2 g HSA in 30 ml of 0.17 M Bic in a molar ratio of 1:1 with pH control and constant stirring, so that the pH value was constantly above 7.5. During the addition of 4-DAPS already, the solution started dyeing red, the color constantly increasing with proceeding reaction time. Contaminations such as excess urea or salts were separated by ultrafiltration via a YM 30 membrane in an Amicon pressure filtration cell. A conjugate consisting of 4-aminophenylsulphonic acid and HSA was obtained, an azo group being present as linker.

The purity of the conjugate according to the invention was checked by means of HPLC (precolumn: Zorbax Diol 20µ (50×4 mm), column 1: Zorbax GF 450, column 2: Zorbax GF 250, eluent: 0.2 M Na citrate, pH 7.5, flow 1 ml/min).

B. Example 2

Preparation Of A Conjugate According To The Invention Consisting Of Human Serum Albumin And 4-Aminophenylphosphonic Acid, An Azo Group Being Present As Linker The preparation of the conjugate and its structure are shown in FIG. 1.

The preparation was carried out as described in Example 1, 4-aminophenylphosphonic acid having been used in place of 4-aminophenylsulphonic acid.

C. Example 3

Preparation Of A Conjugate According To The Invention Which Consists Of Cytidine, A Linker Containing An Azo Group And Human Serum Albumin (Cytidinc-4-DAPS-HSA)

The preparation of the conjugate and its structure are shown in FIG. 2.

4-DAPS was prepared as described in Example 1.
1. Linkage of 4-DAPS to cytidine:
   2.6 mmoles of cytidine (about 600 mg) were dissolved in 6 ml 2 N NaOH, and the 4-DAPS solution was added in portions (1 ml each) with stirring. The initially colorless cytidine solution adopts a more and more intense red color during the addition of 4-DAPS already. After completion of the reaction, the deep-red solution was adjusted with 1 N HCl to a pH value of about 2 and then lyophilized. The dry residue obtained after the lyophilization is subsequently dissolved in a mixture consisting of 8 ml of methanol and 2 ml of DMF and separated from insoluble sediment by filtration. 5(4-diazophenylsulphonic acid) cytidine (5(4-DAPS)cytidine) was obtained.

The purity of the product was checked by means of thin-layer chromatography (plates with fluorescence indicator, eluent: Etac/MeOH 1/1).
2. Activation of 5(4-DAPS) cytidine to form the corresponding HSI ester:
   An aliquot of the solution of 5(4-DAPS) cytidine was admixed in the same solvent (4 parts of methanol and 1 part of DMF) with two times the molar amount of dicyclohexylcarbodiimide (DCC) and 7 to 10 times the molar amount of N-hydroxysuccinimide (HSI). After a reaction time of about 1 h, the activation of the 5(4-DAPS) cytidine into the corresponding HSI ester is terminated. It can be used directly for linkage to HSA.
3. Linkage of the HSI ester of 5(4-DAPS) cytidine to HSA:
   The HSI ester of 5(4-DAPS) cytidine was slowly added to a solution of 2 g HSA in 30 ml 0.17 M Bic with constant stirring. DCC already precipitates during he addition of the HSI ester of 5(4-DAPS) cytidine. The turbid matter of DCC and DC urea was separated by means of filtration. Other contaminations such as methanol, DMF and HSI were then separated via a YM 30 membrane in an Amicon pressure filtration cell. Cytidine-4-DAPS-HSA was obtained.

The purity of the conjugate according to the invention was checked by means of HPLC. See, Example 1, infra.

D. Example 4

Preparation Of A Conjugate According To The Invention Consisting Of UDR, A Linker Containing An Azo Group And Human Serum Albumin (UDR-4-DAPS-HSA)

The conjugate according to the invention was prepared as described in Example 3, UDR having been used in place of cytidine. UDR-4-DAPS-HSA was obtained.

E. Example 5

Preparation Of A Conjugate According To The Invention Consisting Of AraC, A Linker Containing An Azo Group And Human Serum Albumin (AraC-4-DAPS-HSA)

The conjugate according to the invention was prepared as described in Example 3, AraC having been used in place of cytidine. AraC-4-DAPS-HSA was obtained.

F. Example 6

Preparation Of A Conjugate According To The Invention Consisting Of CDR, A Linker Containing An Azo Group And Human Serum Albumin (CDR-4-DAPS-HSA)

The conjugate according to the invention was prepared as described in Example 3, CDR having been used in place of cytidine. CDR-4-DAPS-HSA was obtained.

G. Example 7

Preparation Of A Conjugate According To The Invention Consisting Of 7-Chlorotetra-Cycline, A Linker Containing An Azo Group And Human Serum Albumin The preparation of the conjugate and its structure are shown in FIG. 3.

4-DAPS was prepared as described in Example 1.

1. Linkage of 4-DAPS to 7-chlorotetracycline:

718.5 mg (1.5 mM) of 7-chlorotetracycline (MW 478.9) were dissolved in 20 ml 1 N NaOH, and the 4-DAPS solution was added in portions (1 ml each) with constant stirring. The 7-chlorotetracycline solution initially dyed yellow adopted a more and more intense red color during the addition of 4-DAPS. After a reaction time of about 24 h, the deep-red solution was adjusted to a pH value of about 2 using 1 N HCl and lyophilized. The dry residue was then dissolved in a mixture consisting of 8 ml of MeOH and 2 ml of DMF and separated from the insoluble sediment by filtration. 7-Chloro-9 (4-diazophenylsulphonic acid) tetracycline (4-DAPS-chlorotetracycline) was obtained.

2. Activation of 4-DAPSchlorotetracycline for protein linkage:

An aliquot of the solution of the 4-DAPS-tetracycline was admixed in the same solvent (4 parts of MeOH and 1 part of DMF)—without preceding separation of the excess 7-chlorotetracycline—with two times the molar amount of DCC (based on the employed amount of phenylsulphonic acid) and 7 to 10 times the molar amount of HSI. After a reaction time of about 2 h, the activation of 4-DAPS-chlorotetracycline into the corresponding HSI ester is terminated. The resulting ester can be used directly for protein linkage.

3. Linkage of the HSI ester of 4-DAPSchlorotetracycline to HSA:

The equimolar amount of HSI ester of 4DAPS-chlorotetracycline is slowly added to a solution of 2 g of HSA in 30 ml 0.17 M Bic with constant stiring. The excess of DCC precipitates already during the addition of the HSI ester. The turbid matter of DCC and DC urea was separated by means of filtration prior to pressure filtration. Other contaminations such as MeOH, DMF and HSI were separated via a YM 30 membrane in an Amicon pressure filtration cell. 7-Chloro-9 (4-diazophenylsulphonic acid) tetracycline-HSA was obtained.

The purity of the resulting conjugate was determined by means of HPLC. See, Example 1, infra.

H. Example 8

Preparation Of A Conjugate Consisting Of Tetracycline, A Linker Containing An Azo Group And Human Serum Albumin The conjugate was prepared as described in Example 7, tetracycline having been used in place of 7-chlorotetracyline. The structure of the conjugate is shown in FIG. 3.

I. Example 9

Growth Inhibition Of Tumor Cells By Administration Of Conjugates According To The Invention The conjugates UDR-4-DAPS-HSA (see, Example 4, supra), AraC-4-DAPS-HSA (see, Example 5, supra) and CDR-4-DAPS-HSA (see, Example 6, supra) as well as HSA alone as control were incubated in each case with Walker 256 cells under conventional conditions. The number of cells per ml was determined after 24, 48 and 72 h, respectively.

Figure 4:
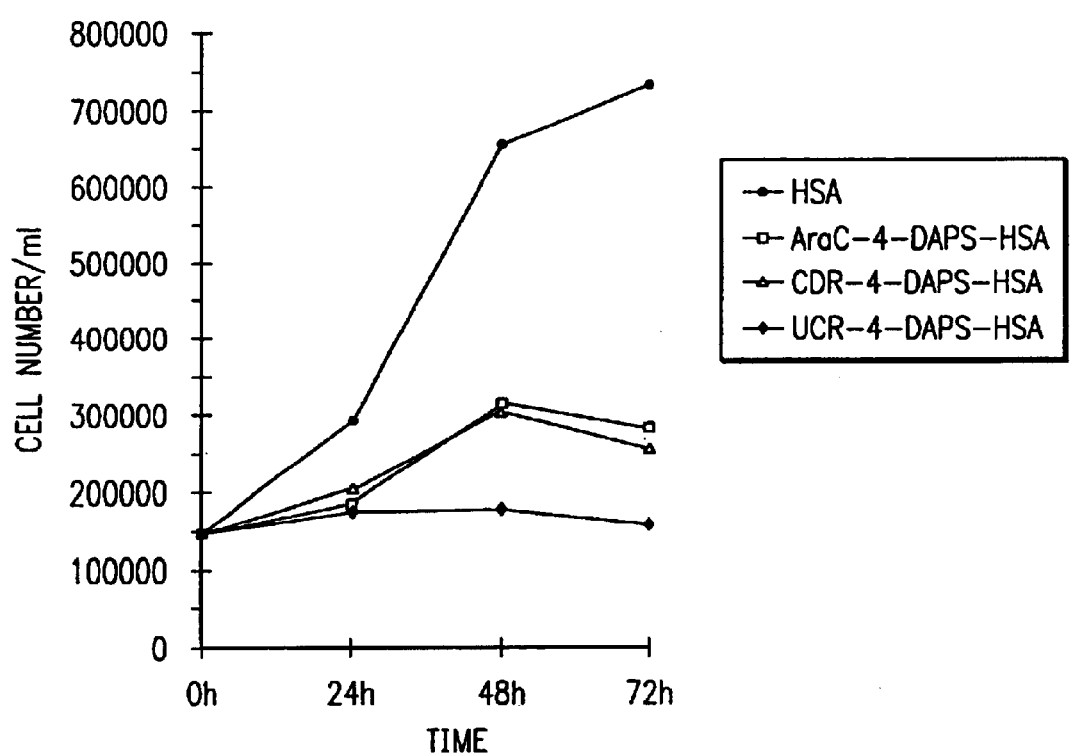
FIG. 4 shows the growth inhibition of tumor cells by administration of conjugates according to the invention.

As follows from FIG. 4, each of the conjugates according to the invention reduces the proliferation of tumor cells as compared to the control.

All references cited within the body of the instant specification are hereby incorporated by reference in their entirety.

What is claimed is:

1. A conjugate useful for treating a disease selected from the group consisting of tumoral, infectious, and autoimmune disease in a subject comprising:

an active substance useful for treating said disease selected from the group consisting of a chemotherapeutic agent and a photoactive compound;

a native human serum albumin that is not regarded as exogenous by the subject; and a linker linking said active substance to said albumin, wherein said linker can be cleaved intracellularly, and wherein said linker comprises an azo group.

2. The conjugate of claim 1, wherein the chemotherapeutic agent is an antibiotic.

3. The conjugate of claim 1, wherein the chemotherapeutic agent is an antimetabolite.

4. The conjugate of claim 1, wherein several active substances useful for treating said disease are linked to said albumin through one or more linkers.

5. The conjugate of claim 1, wherein the linker has the following structure:

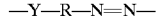

wherein:

R is an aromatic compound, and

Y is selected from the group consisting of C(O), S(O)$_2$, P(O)OH and As(O)OH.

6. The conjugate of claim 1, wherein the conjugate comprises 4-aminophenylsulphonic acid or 4-aminophenylphosphonic acid and albumin.

7. The conjugate of claim 1, wherein the conjugate comprises cytidine.

8. The conjugate according to claim 1, wherein the conjugate comprises tetracycline.

9. A method of treating a disease selected from the group consisting of tumoral infectious, and autoimmune disease, comprising administering the conjugate of claim 1 in an amount effective to ameliorate the symptoms of said disease.

10. The conjugate of claim 1, wherein several active substances are present.

11. The conjugate of claim 1, wherein the linker has the following structure:

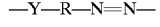

wherein:

R is an aromatic compound, and

Y is a group selected from the group consisting of C(O), S(O)$_2$, P(O)OH and As(O)OH.

12. The conjugate according to claim 4, wherein the linker has the following structure:

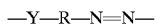

wherein:

R is an aromatic compound, and

Y is a group selected from the group consisting of C(O), S(O)$_2$, P(O)OH and As(O)OH.

13. A process for the preparation of the conjugate of claim 1, comprising binding an active substance selected from the group consisting of a chemotherapeutic agent and a photoactive compound useful for treating a disease selected from the group consisting of tumoral, infectious, and autoimmune disease to a native human serum albumin that is not regarded as exogenous by the subject, by means of a linker containing an azo group, wherein said binding comprises the formation of an ester.

14. The conjugate of claim 2, wherein the antibiotic comprises a tetracycline.

15. The conjugate of claim 3, wherein the antimetabolite comprises a methotrexate.

16. The conjugate of claim 3, wherein the antimetabolite comprises a sulfonamide.

17. The conjugate of claim 3, wherein the antimetabolite comprises a nucleoside that inhibits the replication or transcription of a nucleic acid into which it is incorporated.

18. The conjugate of claim 1, wherein the active substance comprises an acid group.

19. The conjugate of claim 18, wherein the acid group is selected from the group consisting of —CO$_2$H, —SO$_3$H, —PO$_3$H$_2$, and —AsO$_3$H$_2$.

20. The conjugate of claim 1, wherein the active substance is selected from the group consisting of 4-aminobenzoic acid, 2-aminobenzoic acid, 4-aminophenylsulphonic acid, 2-aminophenylsulphonic acid, 4-aininophenylphosphonic acid, 2-aminophenylphosphonic acid, 4-aminophenylarsonic acid, and 2-aminophenylarsonic acid.

21. The conjugate of claim 1, wherein the active substance is selected from the group consisting of a deoxyuridine, a deoxycytidine, a cytosine arabinoside, a 5-fluorouracil, a 5-fluorodeoxyuridine, and an azidothymidine.

22. The conjugate of claim 1, wherein the photoactive compound comprises a porphyrine.

23. The conjugate of claim 1, wherein the photoactive compound is selected from the group consisting of a chlorine and a bacteriochlorine.

24. The conjugate of claim 5, 11 or 12, wherein the aromatic group comprises a phenylene.

25. The conjugate of claim 5, 11 or 12, wherein the aromatic group comprises a derivative of phenylene.

* * * * *